US010391030B2

(12) United States Patent
Gentile et al.

(10) Patent No.: US 10,391,030 B2
(45) Date of Patent: Aug. 27, 2019

(54) RECEPTION, DRAINING AND TRANSFER OF A HIGH QUANTITY OF BIOPHARMACEUTICAL FLUID UNDER PRESSURE WITH A VIEW TO SUBSEQUENT TREATMENT

(71) Applicant: SARTORIUS STEDIM FMT SAS, Aubagne (FR)

(72) Inventors: Cedric Gentile, Aix en Provence (FR); Maurizio Giovani, Chiusdino (IT); Paolo Truzzi, Barberino Val d'Elsa (IT); Laurent Aicardi, Cuges les Pins (FR); Sebastien Svete, Aubagne (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 844 days.

(21) Appl. No.: 14/775,966

(22) PCT Filed: Mar. 13, 2014

(86) PCT No.: PCT/FR2014/050583
§ 371 (c)(1),
(2) Date: Sep. 14, 2015

(87) PCT Pub. No.: WO2014/140494
PCT Pub. Date: Sep. 18, 2014

(65) Prior Publication Data
US 2016/0015599 A1 Jan. 21, 2016

(30) Foreign Application Priority Data
Mar. 13, 2013 (FR) ..................... 13 52246

(51) Int. Cl.
*A61M 5/148* (2006.01)
*A61J 1/10* (2006.01)
(Continued)

(52) U.S. Cl.
CPC ............... *A61J 1/10* (2013.01); *A61J 1/1493* (2013.01); *A61M 5/1486* (2013.01); *B65D 33/01* (2013.01); *B67D 7/0261* (2013.01)

(58) Field of Classification Search
CPC .. A61M 5/1483; A61M 5/1486; A61M 5/152; A61M 5/155; A61M 5/148;
(Continued)

(56) References Cited

U.S. PATENT DOCUMENTS 3,838,794 A 10/1974 Cogley et al.
4,048,994 A * 9/1977 Lo ............................ A61J 1/10
128/DIG. 12
(Continued)

FOREIGN PATENT DOCUMENTS

EP 0077189 * 4/1983
EP 1 923 082 A1 5/2008
(Continued)

OTHER PUBLICATIONS

International Search Report, dated Jun. 17, 2014, from corresponding PCT Application.
(Continued)

*Primary Examiner* — Jill A Warden
*Assistant Examiner* — Dwayne K Handy
(74) *Attorney, Agent, or Firm* — Young & Thompson

(57) ABSTRACT

Device for receiving and draining a high quantity of biopharmaceutical fluid under pressure includes an inner bag, having an inner container for receiving the fluid and provided with a filling port, a drain port, a filling tube having a filling inlet for connection to a filling line, a drain tube having a drain outlet for connection to a drain line, an outer container in which the bag is placed, a compression chamber between the outer container and the bag, an injection port for injecting pressurized draining gas into the chamber, sealed
(Continued)

bushings passing through the container via the filling and drain tubes, the deformation capacities of the bag and container being such that, when the draining gas is injected into the chamber, the bag is compressed and the biopharmaceutical fluid is emptied. The outer container includes a receptacle forming the outer chamber, the tubes passing therethrough via permanently fixed connections.

70 Claims, 4 Drawing Sheets

(51) Int. Cl.
  *B67D 7/02* (2010.01)
  *A61J 1/14* (2006.01)
  *B65D 33/01* (2006.01)

(58) Field of Classification Search
  CPC ...... B01L 3/505; A61J 1/10; A61J 1/14; A61J 1/1493
  See application file for complete search history.

(56) References Cited

U.S. PATENT DOCUMENTS

| | | |
|---|---|---|
| 5,163,909 A | 11/1992 | Stewart |
| 5,399,166 A | 3/1995 | Laing |
| 5,720,728 A * | 2/1998 | Ford ................ A61M 3/0233 604/131 |
| 5,799,830 A | 9/1998 | Carroll et al. |
| 2008/0087489 A1 | 4/2008 | Bruck et al. |
| 2012/0312415 A1 | 12/2012 | Gay et al. |

FOREIGN PATENT DOCUMENTS

| | | |
|---|---|---|
| FR | 2 682 602 A1 | 4/1993 |
| FR | 2 850 582 A1 | 8/2004 |
| FR | 2 956 092 A1 | 8/2011 |
| WO | 2006/122179 A2 | 11/2006 |

OTHER PUBLICATIONS

French Search Report, dated Sep. 24, 2013, from corresponding French Application.

* cited by examiner

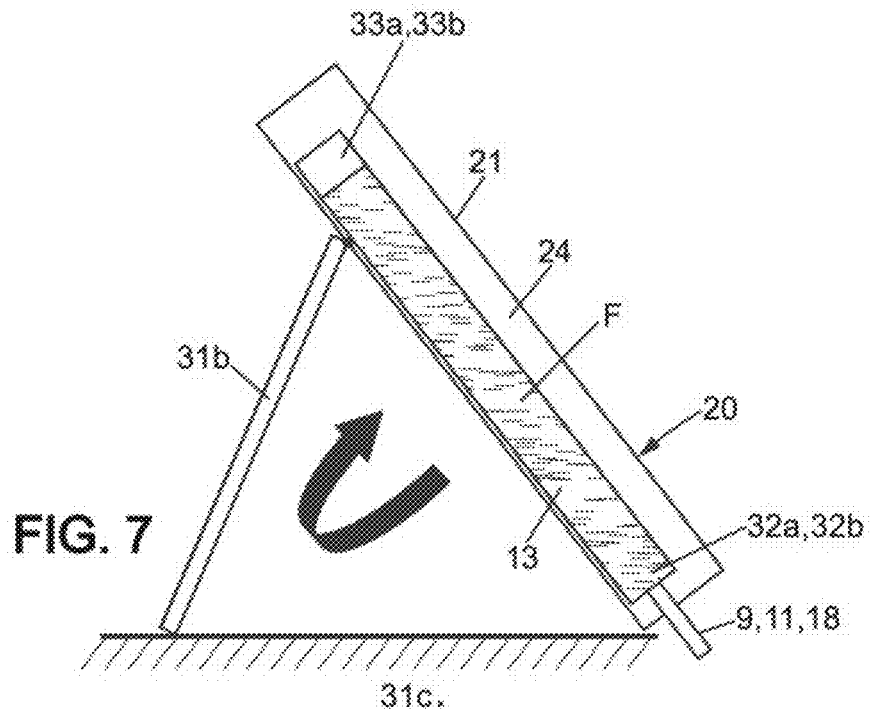
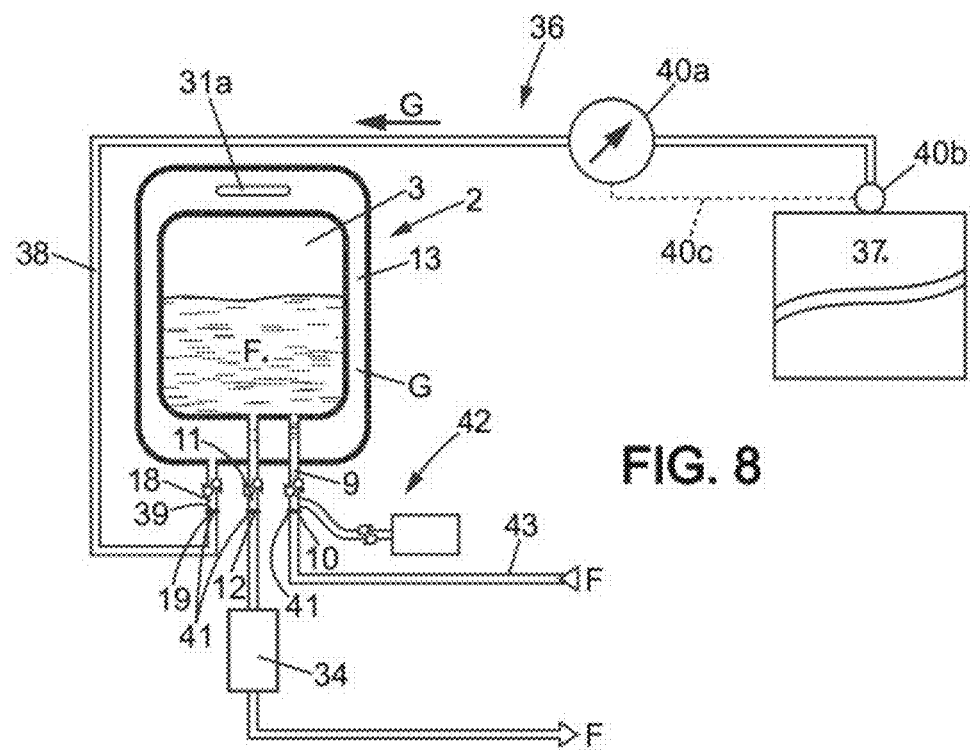

— RECEPTION, DRAINING AND TRANSFER OF A HIGH QUANTITY OF BIOPHARMACEUTICAL FLUID UNDER PRESSURE WITH A VIEW TO SUBSEQUENT TREATMENT

FIELD OF THE INVENTION

The invention relates to the reception and then the draining and transfer of a large amount of biopharmaceutical fluid under controlled pressure, for the purposes of further treatment.

It concerns such a reception and draining device especially intended for this purpose, a system for the reception and transfer of a biopharmaceutical fluid under controlled pressure comprising such a device, and a method for the reception and transfer of a biopharmaceutical fluid under controlled pressure in which such a system is used.

BACKGROUND TO THE INVENTION

In a biopharmaceutical fluid preparation process by a laboratory which prepares pharmaceutical products, it is known to receive a large amount of biopharmaceutical fluid in a sterile container appropriate for this purpose, typically holding about 10 to 20 liters, and then at the desired time to empty the container of the biopharmaceutical fluid and transfer it for further processing, typically filtration or the like, followed by final formulation or the filling of smaller capacity containers. All these operations must be performed fairly quickly for industrial reasons, and in a sterile manner. In addition, if filtration or a similar step is planned, the biopharmaceutical fluid must be under sufficient pressure beforehand to accommodate the loss of pressure at the filter.

The specific field of the invention is the preparation of a biopharmaceutical fluid by a laboratory which prepares pharmaceutical products, where the reception and then the draining and transfer concern a large amount of biopharmaceutical fluid, at least about 10 liters, for the purposes of further treatment such as filtration, final formulation, and/or filling containers of smaller capacity.

For the operations presented above, it is known to make use of a system for the reception and transfer of a biopharmaceutical fluid under controlled pressure, comprising a device for receiving then draining a biopharmaceutical fluid under controlled pressure, a means intended and suitable for supplying a pressurized compression gas having a line for injection of the pressurized compression gas, and a means for monitoring and controlling the pressure of the pressurized compression gas in the injection line. The amounts of biopharmaceutical fluid received then transferred can typically be about a liter or several tens of liters.

In a first known embodiment, the device comprises a rigid receptacle made of stainless steel, provided with a removable cover, forming an inner container intended and suitable for receiving the biopharmaceutical fluid, an inlet for filling the container with the biopharmaceutical fluid, located at the top, an outlet for draining the biopharmaceutical fluid from the container, located at the bottom, and an inlet for the pressurized draining gas. Such a device can be used repeatedly after rigorous cleaning. Such a device has the disadvantages, however, of the cleaning prior to reuse being long and expensive and meticulous, and the draining gas being in contact with the biopharmaceutical fluid which is undesirable in a sterile process.

In a second known embodiment, illustrated by U.S. Pat. No. 5,799,830, the device firstly comprises an inner bag made of flexible and fluidtight plastic, having an inner container intended and suitable for receiving the biopharmaceutical fluid, provided with a port for filling with the biopharmaceutical fluid and a port for draining the biopharmaceutical fluid, and associated with these ports, a filling tube having an inlet for filling the container with biopharmaceutical fluid and drain tube having an outlet for draining biopharmaceutical fluid from the container. The device secondly comprises a rigid external stainless steel container into which the inner container is placed, forming a compression chamber between the external container and the inner container, and the filling tube and drain tube connect, by their inlet and outlet respectively, to the outside of the external container. The external container is provided with a pressurized draining gas injection inlet in the compression chamber. With such a device, the external container can be used repeatedly, as with the first described embodiment, with the inherent disadvantages. Such a device is complex, however, since the external container must include a door for the introduction and removal of the inner bag which it must be possible to open and close in a fluidtight manner, and delivery and draining systems associated in fluid communication with the inner bag and associated in a fixed and fluidtight manner with the external container. This door and these delivery and drainage systems make it even more complex to clean the external container. Finally, the drain tube passes through the inner bag from one side to the other so that when the bag is compressed as much as possible, a residual volume remains within which is difficult or impossible to empty.

In the specific field of the invention, a need therefore exists for the ability to receive and then drain and transfer, under sufficient and controlled pressure, a large amount of biopharmaceutical fluid of at least about 10 liters.

Known from the prior art are devices and methods for the infusion of a liquid into the human body, which typically concern small amounts of liquid, less than 3 liters. Infusion devices relying on simple gravity are well known. There are also devices in which the flow rate is controlled by applying a compaction pressure to the bag containing the liquid to be infused, by means of a chamber filled with a gas as is described for example in U.S. Pat. No. 3,838,794, FR-A-2, 682,602, GB 2,850,582, U.S. Pat. Nos. 5,163,909, 5,399, 166, and EP 1,923,082.

Such devices and methods are not part of the specific field of the invention. With these devices and methods, unlike the field of the invention, the fluid involved is an infusion liquid or a parenteral liquid or similar, only used for delivery to a patient, typically in a healthcare center. Moreover, unlike the field of the invention, the reception and draining involve small amounts, at most 3 liters and usually much less. Finally, compared to the field of the invention, the applied pressures are much lower, and the requirements concerning delivery of the contents after draining are different.

Thus, considering only document U.S. Pat. No. 3,838, 794, that document emphasized clogging of the device due to contact of the walls, a problem that may indeed arise with devices of small capacities and high flexibility but not occurring in the field of the invention where the capacities are much larger and the devices much less flexible.

SUMMARY OF THE INVENTION

A description of the invention as characterized in the claims is presented below.

In a first aspect, based on the prior art of the known second embodiment as previously described, the invention relates to a device for the reception and then the draining of a large amount of a biopharmaceutical fluid, at least equal to about 10 liters, under controlled pressure by a laboratory which prepares pharmaceutical products, for the purposes of further treatment such as filtration, final formulation, and/or filling containers of smaller capacity, comprising:

an inner bag made of plastic, flexible and fluidtight, having an inner container intended and suitable for receiving a quantity at least equal to about 10 liters of biopharmaceutical fluid and provided with a filling port for supplying the biopharmaceutical fluid and a drain port for emptying the biopharmaceutical fluid, and connected in a fluidtight manner to the filling port and drain port, a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid, an outer container into which the inner bag is placed, a compression chamber being formed between the outer container and the inner bag for which the filling inlet and drain outlet are located externally to the outer container, a port for injecting pressurized draining gas into the compression chamber being provided on said outer container, fluidtight passages through the outer container via the filling tube and drain tube, the respective deformation capacities of the inner bag and outer container are chosen such that when injecting the pressurized draining gas into the compression chamber, the inner bag is compressed and the pressure causes the biopharmaceutical fluid contained therein to empty through the drain outlet.

The device according to this first aspect is such that:

the outer container comprises a fluidtight outer receptacle made of plastic, forming an outer chamber into which the inner bag is placed, defining the compression chamber, and comprising the injection port for the pressurized draining gas, the filling tube and drain tube pass through the outer receptacle via fixed permanent connections (35), the filling inlet and drain outlet being located externally to the outer receptacle, it also comprises an integrated means for bleeding the gas filling the filling line prior to filling with biopharmaceutical fluid, so that this gas does not enter the inner bag, the outer receptacle and the inner bag form a coherent whole that is disposable.

In a second aspect, based on the prior art of the known embodiment of the infusion device presented above, the invention relates to a device for the reception and then the draining of a biopharmaceutical fluid under controlled pressure, comprising:

an inner bag made of plastic, flexible and fluidtight, having an inner container intended and suitable for receiving the biopharmaceutical fluid and provided with a filling port for supplying the biopharmaceutical fluid and a drain port for emptying the biopharmaceutical fluid, and connected in a fluidtight manner to the filling port and drain port, a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid, an outer container comprising a fluidtight outer receptacle made of plastic, forming an outer chamber into which the inner bag is placed, its filling inlet and drain outlet being located externally to the outer container, defining a compression chamber between the outer container and the inner bag, a port for injecting pressurized draining gas into the compression chamber being provided on said outer container, the filling tube and drain tube passing through the outer receptacle via fluidtight and fixed permanent connections, the respective deformation capacities of the inner bag and outer container being chosen such that when injecting the pressurized draining gas into the compression chamber, the inner bag is compressed and the pressure causes the biopharmaceutical fluid contained therein to empty through the drain outlet, the outer receptacle and the inner bag forming a coherent whole that is disposable.

The device according to this second aspect is such that:

the inner bag is intended and suitable for receiving an amount at least equal to about 10 liters of biopharmaceutical fluid, and the outer receptacle when deployed has a capacity of at least 40 liters, it comprises a filling tube section and a drain tube section which are located between the end edge section of the inner bag to which they are adjacent and the end edge section of the wall of the outer receptacle through which they pass via fluidtight and fixed permanent connections, the end edge section of the inner bag and the end edge section of the wall of the outer receptacle being next to one another and offset from one another, the edge of the inner bag being offset from the edge of the outer receptacle;

it also comprises an integrated means for bleeding the gas filling the filling line prior to filling with the biopharmaceutical fluid, so that this gas does not enter the inner bag, the device being specially adapted for the reception and then the draining of a large amount of biopharmaceutical fluid, at least equal to about 10 liters, under controlled pressure by a laboratory which prepares pharmaceutical products, for the purposes of further treatment such as filtration, final formulation, and/or filling containers of smaller capacity.

In a first embodiment, the outer container substantially comprises, in particular consists of, the outer receptacle. In particular, the outer receptacle is a flexible outer bag that is non-expandable or expandable with a limited capacity for expansion, or a rigid or semi-rigid shell.

In a second embodiment, the outer container comprises the outer receptacle which is a flexible outer bag, possibly expandable, and an external containment means adapted to receive the outer bag and able to limit the expansion capacity of the outer bag when the pressurized draining gas is being injected into the compression chamber. For example, the containment means comprises two rigid and parallel main walls spaced apart from one another, in particular at a fixed distance, between which is placed the outer bag comprising two main walls on opposite sides, and the free space at the periphery of the two rigid main walls serves as a passage for placing the outer bag or removing it from between the two main walls. If appropriate, the containment means also comprises one or more rigid side walls, rigidly connecting the two main walls.

In one embodiment, the device further comprises, or is adapted to be associated with, a means adapted such that, at least during draining, the draining port is located towards the lower portion of the inner bag, in particular the lowermost portion of the inner bag, which for example is either a means for suspending the device on the end opposite the drain port or a means for tilting the containment means that the outer container comprises.

In one embodiment, the integrated means for bleeding the gas filling the filling line prior to filling with biopharmaceutical fluid is a bag for initially draining the gas filling the filling line, connected by an extrinsic fluid connection to the filling tube, near the inner bag, an opening/closing device being provided on the extrinsic fluid connection and an opening/closing device being provided on the filling tube near the connection to the extrinsic fluid connection and between the latter and the inner bag.

In one embodiment, the filling tube and drain tube pass through the wall of the outer receptacle from one side to the other via fluidtight and fixed permanent connections, welded or the like, formed in an end edge section of this wall by two facing areas of this wall, some portions flat against one another, other portions trapping the filling tube and drain tube between them in a snug fit.

In one embodiment, the wall of the inner bag comprises an end edge section where the filling port and drain port are located adjacent to one another, and the filling tube and drain tube are located adjacent to one another.

In one embodiment, the filling tube and drain tube pass through the wall of the inner bag from the outer side via fluidtight and fixed permanent connections, welded or the like, formed in an end edge section of this wall by two facing areas of this wall, some portions flat against one another, other portions trapping the filling tube and drain tube between them in a snug fit.

In one embodiment, the filling tube and drain tube pass through the wall of the outer receptacle from one side to the other in an end edge section of this wall and pass through the wall of the inner bag from the outer side in an end edge section of said wall, the end edge section of the wall of the outer receptacle and the end edge section of the inner bag extending generally parallel to one another and positioned adjacent to one another.

In one embodiment, the filling tube and drain tube pass through the wall of the outer receptacle from one side to the other in an end edge section of this wall and pass through the wall of the inner bag from the outer side in an end edge section of that wall, the end edge section of the wall of the outer receptacle and the end edge section of the inner bag being arranged next to one another, the filling tube section and the drain tube section that are located between the end edge section of the wall of the outer receptacle and the end edge section of the inner bag being self-supporting and supporting the inner bag.

In one embodiment, the port for injecting pressurized draining gas, which is connected in particular to an injection tube having an injection inlet, is arranged in the wall of the outer receptacle with a fluidtight and fixed permanent connection, by welding or the like, formed in an end edge section of this wall by two facing areas of this wall, some portions flat against one another, other portions defining between them the injection port, in particular trapping the injection tube between them in a snug fit.

According to some possible embodiments, the wall of the outer receptacle comprises an end edge section where the filling tube, the drain tube, the injection port, in particular the injection tube, are located adjacent to one another. And, connected to the filling inlet and/or the drain outlet and/or the injection port or inlet is/are a/some opening/closing device(s) and/or a/some fluid coupling device(s).

According to one embodiment, aside from any biopharmaceutical fluid, the inner container of the inner bag is empty, in particular of tubing.

In one embodiment, aside from the filling tube section and the drain tube section which are located between the end edge section of the wall of the outer receptacle and the end edge section of the inner bag which are arranged next to one another, the inner bag is mounted so as to be unrestrained within the outer receptacle.

In one embodiment, when the draining gas is injected into the compression chamber, the wall of the inner bag and the wall of the outer receptacle the compression chamber are spaced apart from one another along substantially all their lateral periphery.

In one embodiment, the inner bag has a wall comprising two main wall portions opposite one another and the outer receptacle is a bag in which the wall comprises two main wall portions opposite one another, such that when the inner bag and the bag of the outer receptacle are empty, the respective walls and thus the bags themselves can be folded flat in a layered arrangement.

In one embodiment, the outer receptacle is at least partially transparent to allow viewing the inner bag through the wall.

In one embodiment, the deployed inner bag has a capacity of between 8 liters and 60 liters, in particular about 10 to 50 liters, while the deployed outer receptacle has a capacity at least equal to that of the deployed inner bag, in particular at least equal to about 50 liters for a deployed inner bag having a capacity of about 10.

In one embodiment, the device for the reception and then the draining of a biopharmaceutical fluid under controlled pressure comprises a means with pressure loss such as a filter associated in fluid communication with the drain tube or the drain outlet of the inner container of biopharmaceutical fluid.

In one embodiment, the drain tube or the drain outlet of the inner container of biopharmaceutical fluid is without a pump such as a peristaltic pump.

According to a second aspect, the invention relates to a system for the reception and transfer of a biopharmaceutical fluid under controlled pressure, comprising:
  a device for the reception and then the draining of a biopharmaceutical fluid under controlled pressure as just described, in particular comprising a means with pressure loss such as a filter associated in fluid communication with the drain tube or drain outlet of the inner container of biopharmaceutical fluid,
  a means intended and suitable for supplying a pressurized draining gas, having a pressurized draining gas injection line adapted to be associated in fluid communication or associated in fluid communication with the pressurized draining gas injection inlet or port of said device,
  and a means for monitoring and controlling the pressure of the pressurized draining gas in the pressurized draining gas injection line.

According to some embodiments, the means intended and suitable for supplying a pressurized draining gas supplies the draining gas at a pressure equal to at least 70 mbar, more particularly at least 80 mbar, more particularly at least 100 mbar, more particularly at least 200 mbar, more particularly at least 300 mbar, and/or at a pressure equal to at most 600 mbar, more particularly at most 500 mbar.

According to one embodiment, the system for the reception and transfer of a biopharmaceutical fluid under controlled pressure is without a pump, such as a peristaltic pump, connected to the drain tube or the drain outlet of the inner container of biopharmaceutical fluid.

According to a third aspect, the invention relates to a method for the reception and transfer of a biopharmaceutical fluid under controlled pressure, wherein:
- a system is provided for the reception and transfer of a biopharmaceutical fluid under controlled pressure as just described, in the state that is empty of biopharmaceutical fluid and of pressurized draining gas, and a biopharmaceutical fluid to be received and transferred under controlled pressure is also provided,
- when the biopharmaceutical fluid is to be received in the device, first the integrated means for bleeding the gas filling the filling line is used, thus bleeding the gas filling the filing line, then the inner container of the inner bag is filled with biopharmaceutical fluid via the filling inlet, then the filling inlet is placed in the closed state, the drain outlet being in the closed state, and the biopharmaceutical fluid is left in the inner container of the inner bag as long as desired,
- and, when it is desired to transfer the biopharmaceutical fluid from the inner container under controlled pressure:
  - the injection line for pressurized draining gas and the injection inlet for pressurized draining gas of the outer receptacle are connected in fluid communication and the drain outlet is placed in the open state,
  - then the pressurized draining gas is injected into the compression chamber between the outer receptacle and the inner bag, the pressure compressing the inner bag and causing the biopharmaceutical fluid contained therein to drain out.

In one embodiment, a means with pressure loss such as a filter is associated in fluid communication with the drain tube or drain outlet of the inner container of biopharmaceutical fluid.

In one embodiment, while draining, the drain port is placed towards the lower portion of the inner bag, in particular the lowermost portion of the inner bag.

According to one embodiment, the draining gas is injected such that the pressure of the biopharmaceutical fluid in the drain outlet is substantially constant throughout the draining.

According to some embodiments, the draining gas is supplied at a pressure equal to at least 70 mbar, more particularly at least 80 mbar, more particularly at least 100 mbar, more particularly at least 200 mbar, more particularly at least 300 mbar, and/or at a pressure equal to at most 600 mbar, more particularly at most 500 mbar.

In one embodiment, use is made of an integrated means for bleeding the gas filling the filling line comprising a bag for initial draining, an extrinsic fluid connection to the filling tube, an opening/closing device on the extrinsic fluid connection, and an opening/closing device on the filling tube, and in order to bleed the gas filling the filling line prior to filling with biopharmaceutical fluid, the opening/closing device on the filling tube is closed, then while the opening/closing device on the extrinsic fluid connection is open the filling with biopharmaceutical fluid begins, and when the biopharmaceutical fluid reaches the extrinsic fluid connection the opening/closing device on the extrinsic fluid connection is closed and the opening/closing device on the filling tube is opened.

According to some possibilities, the draining gas is supplied and the inner bag is emptied of biopharmaceutical fluid within a period of between about 2 minutes and 10 minutes.

According to one feature, the inner bag is emptied of all the biopharmaceutical fluid.

According to one feature, once the transfer of biopharmaceutical fluid under controlled pressure is completed, the used device is discarded, as it is disposable.

According to one embodiment, use is made of a device for the reception and then the draining of a biopharmaceutical fluid under controlled pressure wherein the outer container comprises a flexible outer bag and an external containment means, the outer bag being placed within the external containment means to limit the expansion capacity of the outer bag when pressurized draining gas is being injected into the compression chamber.

BRIEF DESCRIPTION OF THE DRAWINGS

The drawings in the figures will now be briefly described.

FIG. 7 is a diagram in vertical section showing the device of FIG. 6 assembled with the inner bag inside the containment means, with a means adapted to ensure that the drain port is positioned towards the lower portion of the inner bag, being a means for tilting the containment means that the outer container comprises.

FIG. 8 is a diagram illustrating a system for the reception and transfer of a biopharmaceutical fluid under controlled pressure comprising a device as previously represented, the method for making use of the integrated bleeding means being schematically represented in the figure.

Figure 1:
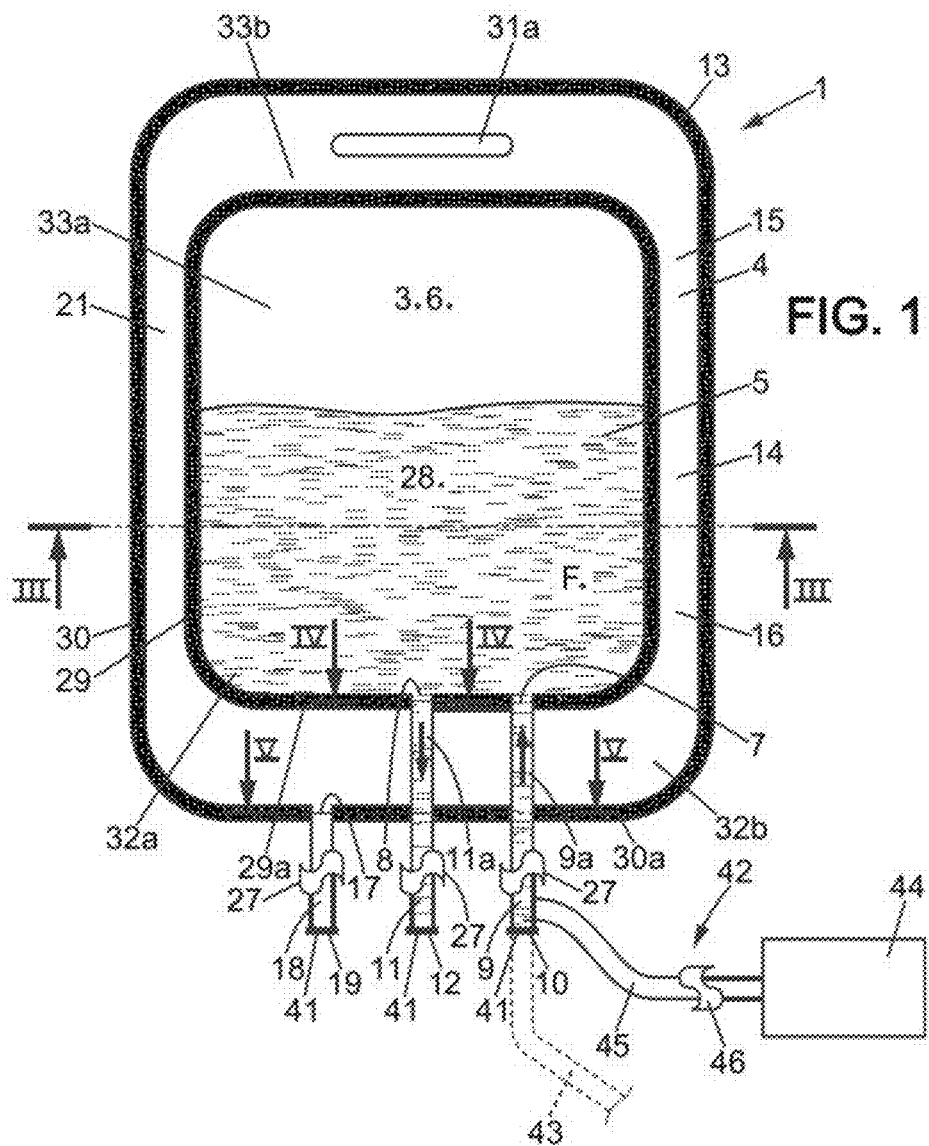
FIG. 1 is an elevational view of a device for the reception and then the draining of a biopharmaceutical fluid under controlled pressure according to the invention, shown flat, empty of biopharmaceutical fluid and draining gas, illustrating the inner bag, the outer container comprising an outer receptacle which is a flexible outer bag itself forming the container or to be associated with an outer container, as in FIG. 6, the compression chamber, the filling tube, the drain tube, the pressurized gas injection port connected to an injection tube, with opening/closing devices, and an integrated bleeding means, the outer receptacle and the inner bag forming a coherent whole that is disposable.

Below is a detailed description of several embodiments of the invention, with examples and with reference to the drawings.

DETAILED DESCRIPTION

The invention relates to a device 1 for the reception and then the draining of a biopharmaceutical fluid under controlled pressure (said device 1 being referred to hereinafter as the "device"), a system 2 for the reception and transfer of a biopharmaceutical fluid under controlled pressure that comprises the device 1 (said system 2 being referred to hereinafter as the "system"), and a method for the reception and transfer of a biopharmaceutical fluid under controlled pressure in which the system 2 is provided and used.

The device 1 comprises an inner bag 3 and outer container 4.

The inner bag 3 is formed from a wall 5 of plastic material. As the wall 5 of the inner bag 3 is flexible and fluidtight, so is the inner bag 3. The inner bag 3 and the wall 5 form and define an inner container 6, which can be flat (FIG. 3A) or deployed (FIGS. 3B and 3C) and which is adapted for receiving biopharmaceutical fluid F.

The inner bag 3 and the wall 5 are provided with a port, in other words a passage, for filling 7 with biopharmaceutical fluid F, and a port, in other words a passage, for draining 8 the biopharmaceutical fluid F. Respectively connected to the filling port 7 and the drain port 8 of the inner bag 3 and the wall 5, in fluidtight and fixed permanent connections, are a filling tube 9 having at its opposite end a filling inlet 10 for filling the inner container 6 with biopharmaceutical fluid F, and a drain tube 11 having at its opposite end a drain outlet 12 for draining the inner container 6 of biopharmaceutical fluid F.

"Fluidtight and fixed permanent connection" is understood to mean a structure such that the wall 5 of the inner bag 3 and the tube 9, 11, in fluid communication with the port 7, 8, are associated with each other such that they do not allow biopharmaceutical fluid F or a gas or possible contaminants to travel between them and such that they form a single inseparable whole.

"Tube" is understood to mean a hollow elongate structure that may be short or long, the term also including a simple port.

Figure 3A:
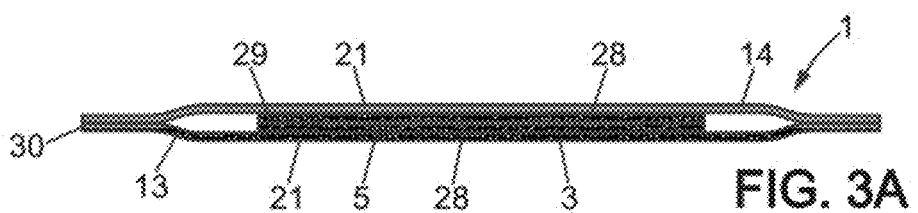
FIG. 3A is an enlarged sectional view of the device of FIG. 1 when flat and empty of biopharmaceutical fluid and draining gas.
Figure 3B:
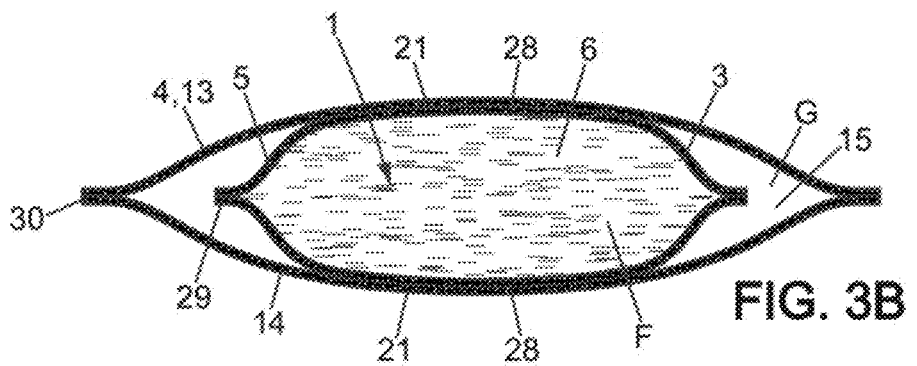
FIG. 3B is a sectional view similar to that of FIG. 3A, with the device no longer flat as the inner bag is now filled with biopharmaceutical fluid, the compression chamber still empty of draining gas.
Figure 3C:
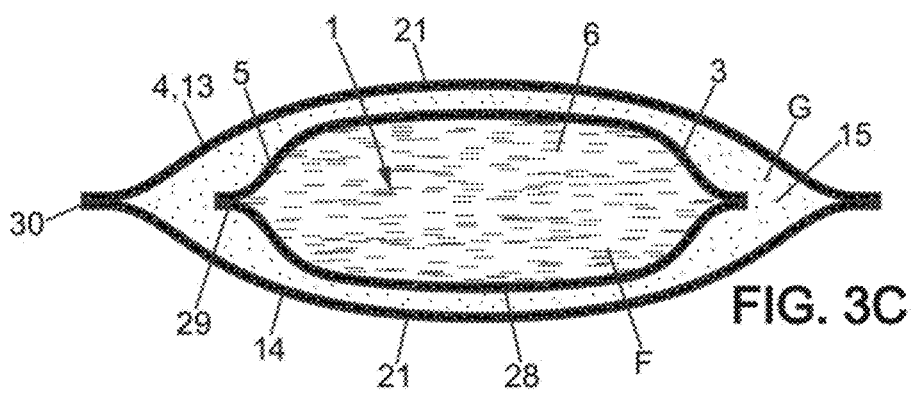
FIG. 3C is a sectional view similar to that of FIGS. 3A and 3B, with the device no longer flat as the inner bag is now filled with biopharmaceutical fluid and the compression chamber is now filled with draining gas.
Figure 4:
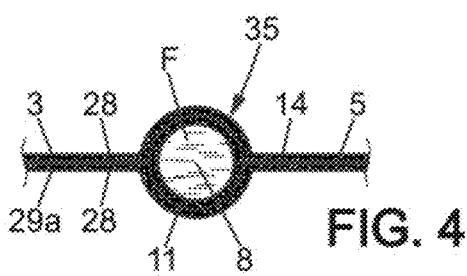
FIGS. 4 and 5 are two sectional views respectively along lines IV-IV and V-V of FIG. 1, illustrating the passage through the inner bag via a fluidtight and fixed permanent connection of a tube, here the filling tube, and the passage through the outer receptacle by fluidtight and fixed permanent connections of the filling tube, the drain tube, and the injection tube.
Figure 5:
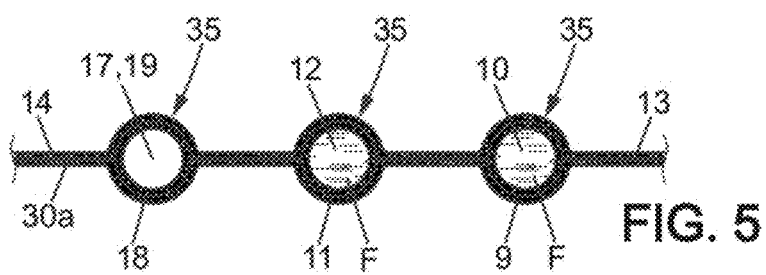

The outer container 4 comprises at least an outer receptacle 13 formed from a wall 14 of plastic material. As the wall 14 of the outer receptacle 13 is flexible and fluidtight, so is the outer receptacle. The receptacle 13 and wall 14 form and define an outer chamber 15, which again can be flat (FIG. 3A) or deployed (FIGS. 3B and 3C).

The outer receptacle 13 of the outer container 4 is intended and suitable for receiving the inner bag 3 (and therefore the inner container 6) in its entirety. Thus the inner bag 3 (and therefore the inner container 6) is placed entirely within, in other words inside, the outer receptacle 13 and the outer chamber 15, or symmetrically, the receptacle 13 is placed so as to surround the outside of the inner bag 3 (and therefore the inner container 6).

A chamber, referred to as the compression chamber 16, is formed in the space between the outer receptacle 13 of the outer container 4 and the inner bag 3.

As a result, the outer receptacle 13 is larger than the inner bag 3, or symmetrically the inner bag 3 is smaller than the receptacle 13. This is true when the inner bag 3 is empty of biopharmaceutical fluid F and the compression chamber 16 of the outer receptacle 13 is empty of draining gas. This is also true when the inner bag 3 is filled with biopharmaceutical fluid F and the compression chamber 16 of the outer receptacle 13 is empty of or filled with draining gas.

The filling inlet 10 and the drain outlet 12 associated with the inner bag 3 are located externally to the outer receptacle 13 so as to be accessible.

The outer receptacle 13 of the outer container 4 is provided with a port, in other words a passage, in fluid communication with the compression chamber 16, for the injection 17 of pressurized draining gas G into the compression chamber 16.

In the embodiment shown, connected to the injection port 17 of the outer receptacle 13 of the outer container 4 and of the wall 14, in a fluidtight and fixed permanent connection (this expression to be understood as defined above), is an injection tube 18 (this term to be understood as defined above) having at its opposite end an injection inlet 19 for injecting draining gas G into the compression chamber 16.

The adjectives "inner" and "outer", respectively applied to the bag 3 and its constituent parts and to the container 4 and receptacle 13, reflect the fact that the receptacle 13 surrounds the outside of the bag 3 which is entirely placed within, in other words inside, the receptacle 13.

The passages through the outer receptacle 13 by the filling tube 9 and drain tube 10 are via fluidtight and fixed permanent connections (this expression to be understood as defined above).

The respective deformation capacities of the inner bag 3 and outer receptacle 13 are chosen such that when injecting the pressurized draining gas G into the compression chamber 16, the inner bag 3 is compressed and the pressure causes the biopharmaceutical fluid F located therein to empty through the drain outlet 12.

Figure 2:
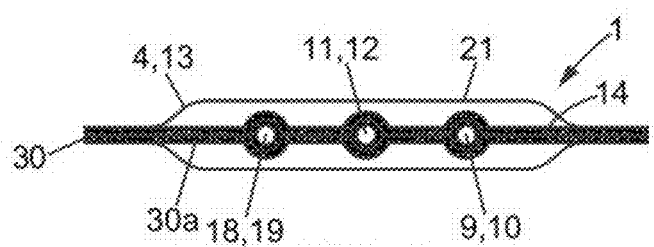
FIG. 2 is an end view of the device shown in FIG. 1.

The inner bag 3 and the outer receptacle 13 are able to be in two extreme states:

a state (the "empty" state) where the inner bag 3 and the outer receptacle 13 both have a small internal volume, in particular as close to zero as permitted by constructional requirements. This is the state where the inner bag 3 and outer receptacle 13 are empty of biopharmaceutical fluid F and draining gas G. In this state, as represented in FIGS. 1, 2, and 3A, the inner bag 3 and the outer receptacle 13 can be folded flat in a layered arrangement.

This is the state of the device 1 after production and before use or at the very beginning of its use. For example, this is the state of the device 1 during storage or transport.

a state (the "filled" state) where the inner bag 3 and the outer receptacle 13 hold a volume of fluid. This is the state where the inner bag 3 is filled with biopharmaceutical fluid F and the outer receptacle 13 is filled with draining gas G, as shown in FIG. 3C. This is the state of the device 1 during use. In this state, the inner bag 3 and the outer receptacle 13 are configured such that the desired amount of biopharmaceutical fluid F fills the inner container 6 and the appropriate amount of pressurized draining gas G fills the compression chamber 16.

As represented in FIG. 3B, it is possible for the device 1 to be in an intermediate state in which the inner bag 3 holds a volume of fluid, being filled with biopharmaceutical fluid F, but the outer receptacle 13 is not filled with draining gas G, so that although the device is deployed, its volume may be only partially expanded and is less than in the situation shown in FIG. 3C.

"Deformation capacity" is understood to mean that both the inner bag 3 and the outer receptacle 13 are each able to be in these two extreme states, and are able to transition from the empty state to the filled state during use of the device 1.

This deformation capacity primarily results from the reshaping of the inner bag 3 and the outer receptacle 13, typically when transitioning from a flat folded and layered configuration to a deployed configuration.

This deformation capacity may also arise from an intrinsic deformation capacity of the walls 5 and 14 of the inner bag 3 and outer receptacle 13, since they may have a certain capacity for expansion, particularly elastic. However, it is understood that the outer receptacle 13 must always fulfill its function of external containment of the inner bag 3, which requires that the expansion capacity of the outer bag 13 be limited when pressurized draining gas G is injected into the compression chamber 16, in particular very low. This may be achieved by a suitable choice of the material or of the complex forming the wall 14 of the outer receptacle 13, or by integrating suitable means into the wall 14 of the outer receptacle 13, such as reinforcing ribs.

With the structure that has just been described, the outer receptacle 13 and the inner bag 3 form a coherent whole that is disposable.

In a first embodiment which can be illustrated by FIG. 1, the outer container 4 essentially comprises, and in particular consists of, the outer receptacle 13. In this first embodiment, the outer receptacle 13 may, in a first variant, be an outer bag 13 which is flexible, and is either non-expandable or is expandable with a limited capacity for expansion. In a second variant, the outer receptacle 13 may be a rigid or semi-rigid shell. In these two variants, the function of external containment of the inner bag 3 is carried out entirely by the outer receptacle 13.

Figure 6:
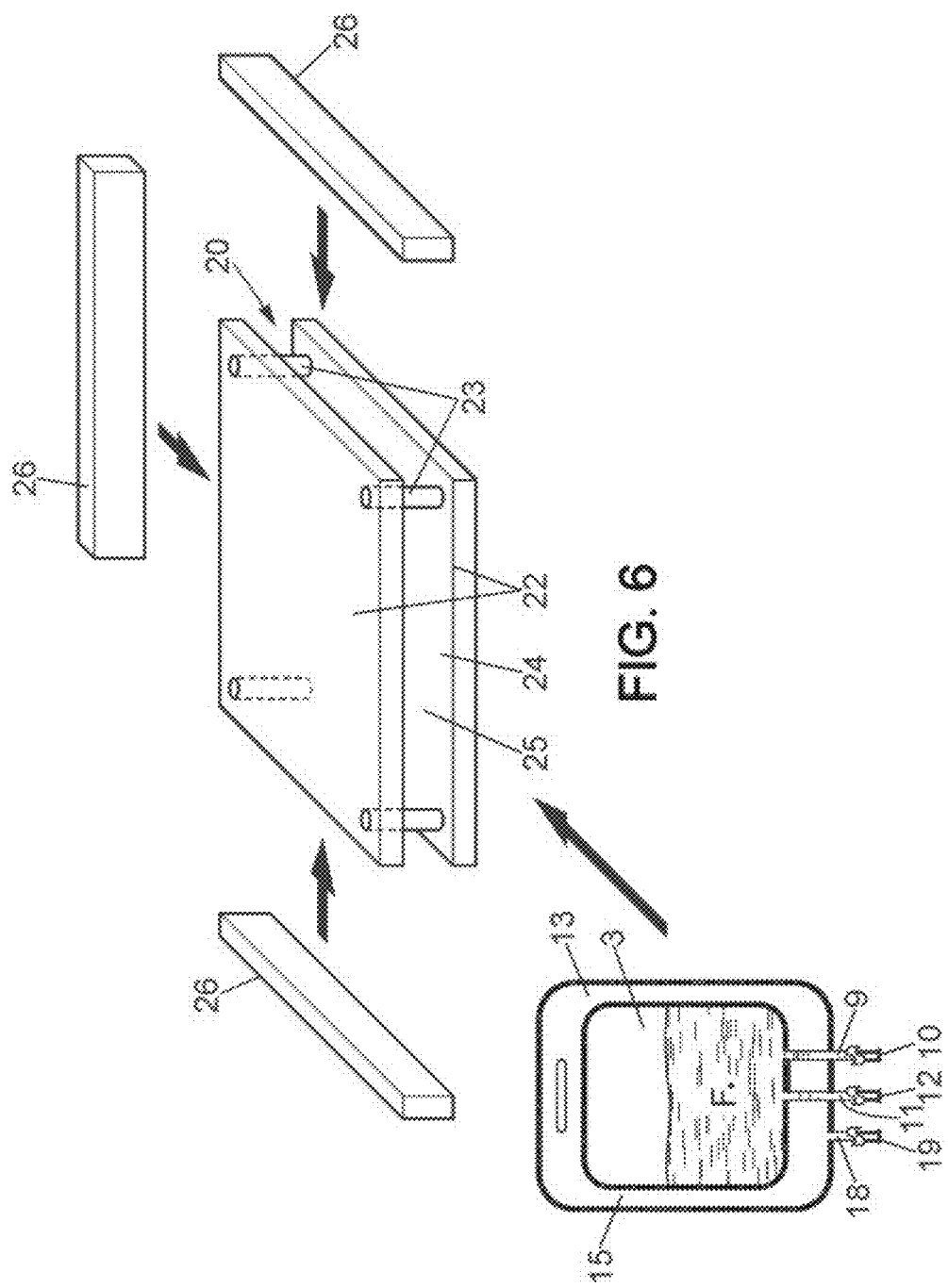
FIG. 6 is a schematic exploded view of the device in the embodiment in which the outer container comprises the outer receptacle which is an outer bag and an external containment means adapted to receive the outer bag and limit the expansion capacity of the outer bag when pressurized draining gas is injected into the compression chamber, the integrated bleeding means having been omitted from the figure.

In a second embodiment, which can be illustrated by FIG. 1 for aspects concerning the outer receptacle 13, the outer container 4 comprises not only the outer receptacle 13 which is a flexible outer bag 13, possibly expandable, but also an external containment means 20, rigid or substantially rigid, this means being illustrated in FIGS. 6 and 7. In this case, the function of external containment of the inner bag 3 is carried out wholly or in part by the external containment means 20.

The outer receptacle 13 and the external containment means 20 are two structurally distinct parts which can cooperate functionally. The external containment means 20 is adapted to receive the outer bag 13. Its function is to limit the expansion capacity of the outer bag 13 when the pressurized draining gas G is injected into the compression chamber 16.

With such external containment means 20, one can be certain that the inner bag 3 is compressed when the pressurized draining gas G is injected into the compression chamber 16, the pressure causing the biopharmaceutical fluid F contained therein to empty through the drain outlet 12.

In one embodiment where the outer bag 13 comprises two main wall portions 21 on opposite sides, the containment means 20 may comprise two rigid main walls 22, parallel to each other, spaced apart from one another (in particular at a fixed distance) by peripheral spacers 23 so as to define a space 24 between them. The outer bag 13 is accommodated within this space 24, so that its two main wall portions 21 press against the two adjacent faces of the walls 22.

The free space 25 at the periphery of the two walls 22 of the containment means 20 acts as a passage for the placement or removal of the outer bag 13 between the two walls 22, in other words said space 24.

Where appropriate, and as represented in FIG. 6, the containment means 20 also comprises one or more rigid side walls 26, adapted for rigid and detachable connection to the two main walls 22 so as to enclose completely or substantially the free space 25, preventing the outer bag 13 from sliding out or protruding through the free space 25 when the draining gas G is injected into the compression chamber 16. This side wall 26, intended for placement next to the tubes 9, 11, and 18, may comprise holes or notches to accommodate these tubes.

Alternatively, such side walls 26 are unnecessary as the outer bag 13 is shaped and designed so that it does not slide out or protrude from the free space 25 during use of the device 1.

The embodiment just described of the containment means 20 is in no way exclusive of other embodiments. In particular, the containment means 20 can be more or less integrated with the outer bag 13, or have a structure other than the structure just described with its wall 22, space 24, space 25, wall 26.

In all cases, the device 1 is arranged so that, when injecting the pressurized draining gas G into the compression chamber 16, the inner bag 3 is compressed by the pressurized draining gas G, the pressure causing the biopharmaceutical fluid F contained therein to empty through the drain outlet 12.

In one embodiment, connected to the filling inlet 10, drain outlet 12, injection inlet 19 is an opening/closing device 27 (FIG. 1) and/or a fluid coupling device 41, adapted to be fluidly coupled in a fixed and fluidtight manner respectively to a filling line 43, a pressurized draining gas G injection line 38 when the device 1 is incorporated into the system 2 and is in use (see FIG. 8). Such opening/closing and fluid coupling devices 27, 41 are known to persons skilled in the art of bag and tube systems for the biopharmaceutical industry.

In the embodiment represented, the inner bag 3 has a wall 5 comprising two main wall portions 28, on opposite sides, fluidtight and permanently fixed together by welding or the like at their common peripheral edge which is also the peripheral edge 29 of the inner bag 3. Similarly, the outer receptacle 13 is then an outer bag 13 of which its wall 14 comprises two main wall portions 21, as has been previously discussed, on opposite sides, fluidtight and permanently fixed together by welding or the like at their common peripheral edge which is also the peripheral edge 30 of the receptacle or outer bag 13. In this case, "outer receptacle" and "outer bag" can be considered to be synonymous.

With such an embodiment, when the inner bag 3 and outer bag 13 are empty, the respective walls 5, 14, as well as the bags 3, 13 themselves, can be folded flat into a layered arrangement as shown in FIGS. 1, 2, and 3A ("empty" state) where the peripheral edges 29 and 30 form rectangles with rounded corners (as is known to those skilled in the art for bags in the biopharmaceutical field), the edge 29 of the inner bag 3 being contained within the edge 30 of the outer bag 13 and the two edges 29 and 30 offset from one another and at least substantially parallel.

When the inner bag 3 is filled with biopharmaceutical fluid F and the outer bag 13 is filled with draining gas G that has been injected into it (filled state), the two bags 3, 13 are deployed, the main portions 28 of the inner bag 3 may not be in contact with the main portions 21 of the bag of the outer receptacle 13 but for example may only be close to them, the draining gas G then completely surrounding the inner bag 3 and the deformation capacities of the inner bag 3 and outer receptacle 13 relative to each other being such that the pressurized draining gas G effectively compresses the inner bag 3, even if the outer receptacle 13 is itself expanded. This implementation is represented in FIG. 3C.

However, it is also possible that the main portions 28 of the inner bag 3 are at least partly pressing against (by their faces directed outward) the main portions 21 of the bag of the outer receptacle 13 (on their faces directed inward), the wall 5 of the inner bag 3 and the wall 14 of the outer bag 13 being spaced apart from one another along all or substantially all their lateral periphery (in other words outside the main portions 28 and 21). Such a configuration corresponds to that of FIG. 3B, it being understood that there is draining gas G in the compression chamber here, which is not the case in the context of FIG. 3B.

In one embodiment, the outer receptacle 13 (or outer bag) is at least partially transparent to allow viewing the inner bag 3 through the wall 14. If there is such, the external containment means 20 is also at least partially transparent.

The device 1 may be provided with labeling that can be read from outside the outer receptacle 13.

In one embodiment, the deployed inner bag 3 has a capacity of between 8 liters and 60 liters, in particular about 10 to 50 liters, depending on the requirements and applications.

The deployed outer receptacle 13 has a capacity at least equal to that of the deployed inner bag 3. Thus, and by way of illustration, the deployed outer receptacle 13 may have a capacity of at least about 50 liters for a deployed inner bag having a capacity of about 10.

According to one constructional arrangement, shown in FIGS. 1 and 7, the device 1 is such that it comprises or is capable of being associated with a means 31a, 31b which itself is adapted so that, at least while draining the biopharmaceutical fluid F, the drain port 8 is positioned toward the lower portion 32a of the inner bag 3 and of the inner container 6 and, in particular, the lowermost portion. This is to ensure that the air in the upper portion 33a of the inner bag 3 and inner container 6 cannot exit through the drain port 8, for safety reasons.

In one possible embodiment (FIG. 1), this means 31a is a means 31a for suspending the device 1, located on the end opposite the drain port 8, such as a suspension eyelet provided in the upper portion 33b of the outer receptacle 13, or possibly in the upper portion 33a of the inner bag 3. The device 1 can thus be arranged vertically with the drain port 8 at the bottom.

According to another possible embodiment (FIG. 7), this means 31b is a means 31b for tilting the compression means 20 which is comprised in the device 1. This tilting means 31b may have one or more legs, for example hinged, associated with one or two walls 22, and the opposite end resting on a horizontal supporting surface 31c. The device 1 can thus be arranged at an incline relative to the horizontal, with the drain port 8 at the bottom.

These two embodiments of the means 31a, 31b, adapted so that the drain port 8 is positioned toward the lower portion, in particular the lowermost portion 32a, of the inner bag 3, at least while draining the biopharmaceutical fluid F, do not exclude other embodiments.

It is understood that the terms "lower", "upper", and "bottom" are understood to be in relation to the device 1 when positioned for usage.

The device 1 also comprises an integrated means 42 for bleeding the gas filling the filling line 43 prior to filling with biopharmaceutical fluid, so that this gas does not enter the inner bag, In one possible embodiment illustrated in FIG. 1, the integrated bleeding means 42 firstly comprises a bag 44 for initially draining the gas filling the filling line 43, connected by an extrinsic fluid connection 45 to the filling tube 9, near the inner bag 3, for example near the filling inlet 10 and the opening/closing device 27 provided on the filling tube 9 near the filling inlet 10.

The initial draining bag 44 has the capacity to receive all of the gas filling the filling line. Such a bag can be flexible and made of plastic, similarly to the inner bag 3.

The integrated bleeding means 42 next comprises an opening/closing device 46 on the extrinsic fluid connection 45 between the bag 44 and the filling tube 9. As already indicated, an opening/closing device 27 for the filling tube is also provided at or near the connection with the extrinsic fluid connection 45 and between the latter and the inner bag 3.

In the embodiment represented, the draining bag 44 is positioned outside the receptacle 13.

In one application of the device 1 and the system 2, for the purposes of a filtration or similar step followed by a step of final formulation or of the filling of small containers, a means with pressure loss 34 is provided, such as a filter, associated in fluid communication with the tube 11 or outlet 12 for draining the inner container 6 of biopharmaceutical fluid F.

With the pressures concerned for the draining gas G, it is possible to empty an inner bag 3 as described of the amount of biopharmaceutical fluid F located within the inner container 6 and force the fluid through the filter 34 within a fairly short time, and with no need for a pump such as a peristaltic pump associated with the drain tube 11 or drain outlet 12. Thus, another characteristic of the device 1 is that the drain tube 11 or drain outlet 12 can be without a pump such as a peristaltic pump.

In the embodiment shown, where the two peripheral edges 29 and 30 have rectangular contours, these may comprise two end edge sections 29a and 30a located respectively at said lower portions 32a and 32b of the inner bag 2 and outer receptacle 13. These two end edge sections 29a, 30a run generally parallel to each other and adjacent to one another, arranged near and separate from one another.

The filling tube 9 and drain tube 11 pass through the wall 5 of the inner bag 3 from the outer side (meaning from end edge section 30a of the outer receptacle 13) via fluidtight and fixed permanent connections 35 formed in end edge section 29a. In particular, the filling port 7 and drain port 8 are located adjacent to one another in end edge section 29a, the filling tube 9 and drain tube 11 being positioned adjacent to one another.

The filling tube 9 and drain tube 11 then pass through the wall 14 of the outer receptacle 13 from one side to the other via fluidtight and fixed permanent connections 35, formed in end edge section 30a.

In addition, the injection port 17, with the injection tube 18, is provided in, respectively passes through, the wall 14 of the outer receptacle 13 via a fluidtight and fixed permanent connection 35 also formed in end edge section 30a.

The filling tube 9, drain tube 11, injection port 17, with injection tube 18, are located in end edge section 30a, adjacent to one another.

With the arrangement described, the device 1 comprises a filling tube 9 section 9a and a drain tube 11 section 11a, located between the end edge section 29a of the inner bag 3 to which they are adjacent and the end edge section 30a of the wall 14 of the outer receptacle 13 which they pass through via fluidtight and fluid permanent connections 35. These filling tube 9 and drain tube 11 sections 9a and 11a are for example self-supporting and support the inner bag 3 within the outer receptacle 13, with no need for directly associating the inner bag 3 and outer receptacle 13 for example attaching their main walls together with the disadvantages inherent thereto (difficult implementation, risk of leakage, extra thickness). In addition, the inner bag 3 is offset from the outer receptacle 13 in the direction of the ports 7, 8 and 17, which does not interfere with the passage of biopharmaceutical fluid F and draining gas G. Also, the draining gas G surrounds the inner bag 3 near ports 7 and 8 near ports 7 and 8. These various structural arrangements contribute to the effectiveness and efficiency of the device 1 and system 2.

A fluidtight and fixed permanent connection 35 such as the one mentioned above can be achieved by welding or the like in the end edge section 29a, 30a concerned, by two facing areas of the wall concerned 5, 14, some portions flat against one another, other portions defining between them a port such as 7, 8, 17 and/or trapping a tube such as 9, 11 18 between them in a snug fit.

In the embodiment of the device 1 represented, aside from any biopharmaceutical fluid F, the inner container 6 of the inner bag 5 is empty, in particular of tubing. Similarly, apart from the filling tube 9 section 9a and the drain tube 11 section 11a, the compression chamber 16 is empty, the inner bag 3 being mounted unrestrained within the outer receptacle 13.

The system 2 firstly comprises the device 1 for the reception and then the draining of a biopharmaceutical fluid F under controlled pressure as just described. In particular, the device 1 has a means with pressure loss such as a filter 34.

The system 2 next comprises a means 36 intended and suitable for supplying the pressurized draining gas G including a source 37 of pressurized draining gas G and an injection line 38 for injecting pressurized draining gas G, adapted to be associated in fluid communication or associated in fluid communication at the outlet 39 with the pressurized draining gas G injection inlet 19 or port 17 of the device 1.

The system 2 also comprises a means 40a, 40b, 40c for monitoring and controlling the pressure of the pressurized draining gas G in the injection line 38, so as to control the injection when such is desired and to control the injection at the desired pressure. Such a means 40a, 40b, 40c may comprise, for example, a pressure gauge 40a, an adjustable valve 40b, and a control line 40c between these.

The pressurized draining gas G is supplied at a pressure at least equal to 70 mbar and at most equal to 600 mbar.

More particularly and depending on requirements, this pressure is equal to at least 80 mbar, more particularly at least 100 mbar, more particularly at least 200 mbar, more particularly at least 300 mbar, and is more particularly equal to at most 500 mbar.

The system 2 also comprises or is associated with the filling line 43 already mentioned.

The method for the reception and transfer of a biopharmaceutical fluid F under controlled pressure according to the invention is such that a system 2 as described is provided, in the empty state containing no biopharmaceutical fluid F and pressurized draining gas G. Also provided is a biopharmaceutical fluid F to be received and transferred under controlled pressure. Pressurized draining gas G is provided via the means 36.

When the biopharmaceutical fluid F is to be received in the device 1, first the integrated means 42 for bleeding the gas filling the filling line 43 is utilized, which bleeds the gas filling the filling line 43.

Next, the inner container 6 of the inner bag 3 is filled with biopharmaceutical fluid F via the filling inlet 10, and then the filling inlet 10 is placed in the closed state, the drain outlet 12 also being in the closed state.

The biopharmaceutical fluid F can be left in the inner container 6 of the inner bag 3 as long as desired, for example for storing, shipping, and/or handling.

When it is desired to transfer the biopharmaceutical fluid F under controlled pressure from the inner container 6 of the inner bag 3, the line 38 for injecting pressurized draining gas G (and in particular its outlet 39) is connected in fluid communication to the inlet 19 for injecting pressurized draining gas G of the outer receptacle 13, and the drain outlet 12 is placed the open state. Next, the pressurized draining gas G is injected into the compression chamber 16 between the outer receptacle 13 and the inner bag 3, the pressure compressing the inner bag 3 and thereby emptying it of the biopharmaceutical fluid F contained therein.

To make use of the integrated bleeding means 42 which comprises the initial draining bag 44, the extrinsic fluid connection 45, the opening/closing device 46, and the opening/closing device 27 on the filling tube 9, in order to bleed the gas filling the filling line 38, the procedure is as follows: before filling the device 1 with biopharmaceutical fluid F, opening/closing device 27 on the filling tube 9 is closed; then while opening/closing device 46 is open the filling with biopharmaceutical fluid F begins; and when the biopharmaceutical fluid F reaches the extrinsic fluid connection 45 opening/closing device 46 is closed and opening/closing device 27 on the filling tube 9 is opened.

As shown, a means with pressure loss such as a filter 14 can be associated in fluid communication with the drain tube 11 or the drain outlet 12.

During draining, the drain port 8 can be placed towards the lower portion 32a of the inner bag 3, in particular the lowermost portion.

According to one embodiment, the draining gas G is injected such that the pressure of the biopharmaceutical fluid F in the drain outlet 12 is substantially constant throughout the draining.

With the pressure of the pressurized draining gas G as previously indicated, an inner bag 3 as described can be emptied within a period of between about 2 minutes and 10 minutes. The inner bag 3 can be emptied of all biopharmaceutical fluid F. After the transfer of biopharmaceutical fluid F under controlled pressure is completed, the used device 1 can be discarded since it is disposable.

In the case where use is made of a device 1 in which the outer container 4 comprises a flexible outer bag 13 and an external containment means 20, the outer bag 13 is placed within the containment means 29 to limit the expansion capacity of the outer bag 13 when injecting pressurized draining gas G into the compression chamber 16.

The invention claimed is:

1. A device for the reception and then the draining of a large amount of biopharmaceutical fluid, at least equal to about 10 liters, under controlled pressure by a laboratory which prepares pharmaceutical products, for the purposes of further treatment such as filtration, final formulation, and/or filling containers of smaller capacity, wherein the device comprises:

an inner bag made of plastic, flexible and fluidtight, having an inner container intended and suitable for receiving a quantity at least equal to about 10 liters of biopharmaceutical fluid and provided with a filling port for supplying the biopharmaceutical fluid and a drain port for emptying the biopharmaceutical fluid, and connected in a fluidtight manner to the filling port and drain port, a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid, an outer container into which the inner bag is placed, a compression chamber being formed between the outer container and the inner bag for which the filling inlet and drain outlet are located externally to the outer container, a port for injecting pressurized draining gas into the compression chamber being provided on said outer container, fluidtight passages through the outer container via the filling tube and drain tube, an integrated means for bleeding the gas filling the filling line prior to filling with biopharmaceutical fluid, so that this gas does not enter the inner bag, and the respective deformation capacities of the inner bag and outer container being chosen such that when injecting the pressurized draining gas into the compression chamber, the inner bag is compressed and the pressure causes the biopharmaceutical fluid contained therein to empty through the drain outlet, wherein:

the outer container comprises a fluidtight outer receptacle made of plastic, forming an outer chamber into which the inner bag is placed, defining the compression chamber, and comprising the injection port for the pressurized draining gas, the filling tube and drain tube pass through the outer receptacle via fixed permanent connections, the filling inlet and drain outlet being located externally to the outer receptacle, and the outer receptacle and the inner bag form a coherent whole that is disposable.

2. A device for the reception and then the draining of a biopharmaceutical fluid under controlled pressure, wherein the device comprises:

an inner bag made of plastic, flexible and fluidtight, having an inner container intended and suitable for receiving the biopharmaceutical fluid and provided with a filling port for supplying the biopharmaceutical fluid and a drain port for emptying the biopharmaceutical fluid, and connected in a fluidtight manner to the filling port and drain port, a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid, an outer container comprising a fluidtight outer receptacle made of plastic, forming an outer chamber into which the inner bag is placed, its filling inlet and drain outlet (12) being located externally to the outer container, defining a compression chamber between the outer container and the inner bag, a port for injecting pressurized draining gas into the compression chamber being provided on said outer container, the filling tube and drain tube passing through the outer receptacle via fluidtight and fixed permanent connections, the respective deformation capacities of the inner bag and outer container being chosen such that when injecting the pressurized draining gas into the compression chamber, the inner bag is compressed and the pressure causes the biopharmaceutical fluid contained therein to empty through the drain outlet, an integrated means for bleeding the gas filling the filling line prior to filling with biopharmaceutical fluid, so that this gas does not enter the inner bag, and and the outer receptacle and the inner bag forming a coherent whole that is disposable, wherein:

the inner bag is intended and suitable for receiving an amount at least equal to about 10 liters of biopharmaceutical fluid, and the outer receptacle when deployed has a capacity of at least 40 liters, the device comprises a section of filling tube and a section of drain tube which are located between the end edge section of the inner bag to which they are adjacent and the end edge section of the wall of the outer receptacle through which they pass via fluidtight and fixed permanent connections, the end edge section of the inner bag and the end edge section of the wall of the outer receptacle being arranged next to and offset from one another, and the device being specially adapted for the reception and then the draining of a large amount of biopharmaceutical fluid, at least about 10 liters, under controlled pressure by a laboratory which prepares pharmaceutical products, for the purposes of further treatment such as filtration, final formulation, and/or filling containers of smaller capacity.

3. The device for the reception and then the draining of a biopharmaceutical fluid under controlled pressure according to claim 1, wherein the outer container consists of the outer receptacle.

4. The device for the reception and then the draining of a biopharmaceutical fluid under controlled pressure according to claim 3, wherein the outer receptacle is a flexible outer bag that is non-expandable or expandable with a limited capacity for expansion.

5. The device for the reception and then the draining of a biopharmaceutical fluid under controlled pressure according to claim 3, wherein the outer receptacle is a rigid or semi-rigid shell.

6. The device for the reception and then the draining of a biopharmaceutical fluid under controlled pressure according to claim 1, wherein the outer container comprises the outer receptacle which is a flexible outer bag, possibly expandable, and an external containment means adapted to receive the outer bag and able to limit the expansion capacity of the outer bag when the pressurized draining gas is being injected into the compression chamber.

7. The device for the reception and then the draining of a biopharmaceutical fluid under controlled pressure according to claim 6, wherein the containment means comprises two rigid and parallel main walls spaced apart from one another, in particular at a fixed distance, between which is placed the outer bag comprising two main walls on opposite sides.

8. The device for the reception and then the draining of a biopharmaceutical fluid under controlled pressure according to claim 7, wherein the free space at the periphery of the two rigid main walls serves as a passage for placing the outer bag or removing it from between the two main walls.

9. The device for the reception and then the draining of a biopharmaceutical fluid under controlled pressure according to claim 7, wherein the containment means also comprises one or more rigid side walls, rigidly connecting the two main walls.

10. The device for the reception and then the draining of a biopharmaceutical fluid under controlled pressure according to claim 1, further comprising, or adapted to be associated with, a means adapted such that, at least during draining, the drain port is located towards the lower portion of the inner bag, in particular the lowermost portion of the inner bag.

11. The device for the reception and then the draining of a biopharmaceutical fluid under controlled pressure according to claim 10, wherein the means adapted such that the drain port is located towards the lower portion of the inner bag is either a means for suspending the device on the end opposite the drain port or a means for tilting the containment means that the outer container comprises.

12. The device for the reception and then the draining of a biopharmaceutical fluid under controlled pressure according to claim 1, wherein the integrated means for bleeding the gas filling the filling line prior to filling with biopharmaceutical fluid is a bag for initially draining the gas filling the filling line, connected by an extrinsic fluid connection to the filling tube, near the inner bag, an opening/closing device being provided on the extrinsic fluid connection and an opening/closing device being provided on the filling tube near the connection to the extrinsic fluid connection and between the latter and the inner bag.

13. The device for the reception and then the draining of a biopharmaceutical fluid under controlled pressure according to claim 1, wherein the filling tube and drain tube pass through the wall of the outer receptacle from one side to the other via fluidtight and fixed permanent connections, welded or the like, formed in an end edge section of this wall by two facing areas of this wall, some portions flat against one another, other portions trapping the filling tube and drain tube between them in a snug fit.

14. The device for the reception and then the draining of a biopharmaceutical fluid under controlled pressure according to claim 1, wherein the wall of the inner bag comprises an end edge section where the filling port and drain port are located adjacent to one another, and the filling tube and drain tube are located adjacent to one another.

15. The device for the reception and then the draining of a biopharmaceutical fluid under controlled pressure according to claim 1, wherein the filling tube and drain tube pass through the wall of the inner bag from the outer side via fluidtight and fixed permanent connections, welded or the like, formed in an end edge section of this wall by two facing areas of this wall, some portions flat against one another, other portions trapping the filling tube and drain tube between them in a snug fit.

16. The device for the reception and then the draining of a biopharmaceutical fluid under controlled pressure according to claim 1, wherein the filling tube and drain tube pass through the wall of the outer receptacle from one side to the other in an end edge section of this wall and pass through the wall of the inner bag from the outer side in an end edge section of that wall, the end edge section of the wall of the outer receptacle and the end edge section of the inner bag extending generally parallel to one another and positioned adjacent to one another.

17. The device for the reception and then the draining of a biopharmaceutical fluid under controlled pressure according to claim 1, wherein the filling tube and drain tube pass through the wall of the outer receptacle from one side to the other in an end edge section of this wall and pass through the wall of the inner bag from the outer side in an end edge section of that wall, the end edge section of the wall of the outer receptacle and the end edge section of the inner bag being arranged next to one another, the section of filling tube and the section of draining tube that are located between the end edge section of the wall of the outer receptacle and the end edge section of the inner bag being self-supporting and supporting the inner bag.

18. The device for the reception and then the draining of a biopharmaceutical fluid under controlled pressure according to claim 1, wherein the port for injecting pressurized draining gas, which is connected in particular to an injection tube having an injection inlet, is arranged in the wall of the outer receptacle with a fluidtight and fixed permanent connection, by welding or the like, formed in an end edge section of this wall by two facing areas of this wall, some portions flat against one another, other portions defining between them the injection port, in particular trapping the injection tube between them in a snug fit.

19. The device for the reception and then the draining of a biopharmaceutical fluid under controlled pressure according to claim 1, wherein the wall of the outer receptacle comprises an end edge section where the filling tube, the drain tube, the injection port, in particular the injection tube, are located adjacent to one another.

20. The device for the reception and then the draining of a biopharmaceutical fluid under controlled pressure according to claim 1, wherein, aside from the section of filling tube and the section of drain tube which are located between the end edge section of the wall of the outer receptacle and the end edge section of the inner bag which are arranged next to one another, the inner bag is mounted so as to be unrestrained within the outer receptacle.

21. The device for the reception and then the draining of a biopharmaceutical fluid under controlled pressure according to claim 1, wherein, when the draining gas is injected into the compression chamber, the wall of the inner bag and the wall of the outer receptacle the compression chamber are spaced apart from one another along all or substantially all their lateral periphery.

22. The device for the reception and then the draining of a biopharmaceutical fluid under controlled pressure according to claim 1, wherein the inner bag has a wall comprising two main wall portions opposite one another and the outer receptacle is a bag in which the wall comprises two main wall portions opposite one another, such that when the inner bag and the bag of the outer receptacle are empty, the respective walls and thus the bags themselves can be folded flat in a layered arrangement.

23. The device for the reception and then the draining of a biopharmaceutical fluid under controlled pressure according to claim 1, wherein the outer receptacle is at least partially transparent to allow viewing the inner bag through the wall.

24. The device for the reception and then the draining of a biopharmaceutical fluid under controlled pressure according to claim 1, wherein the deployed inner bag has a capacity of between 8 liters and 60 liters, in particular about 10 to 50 liters, while the deployed outer receptacle has a capacity at least equal to that of the deployed inner bag, in particular at least equal to about 50 liters for a deployed inner bag having a capacity of about 10.

25. The device for the reception and then the draining of a biopharmaceutical fluid under controlled pressure according to claim 1, comprising a means with pressure loss such as a filter associated in fluid communication with the drain tube or the drain outlet of the inner container of biopharmaceutical fluid.

26. The device for the reception and then the draining of a biopharmaceutical fluid under controlled pressure according to claim 1, wherein the drain tube or the drain outlet of the inner container of biopharmaceutical fluid is without a pump such as a peristaltic pump.

27. A system for the reception and transfer of a biopharmaceutical fluid under controlled pressure, comprising:
a device for the reception and then the draining of a biopharmaceutical fluid under controlled pressure according to claim 1, in particular comprising a means with pressure loss such as a filter associated in fluid communication with the drain tube or drain outlet of the inner container of biopharmaceutical fluid,
a means intended and suitable for supplying a pressurized draining gas, having a pressurized draining gas injection line adapted to be association in fluid communication or associated in fluid communication with the pressurized draining gas injection inlet or port of said device, and
a means for monitoring and controlling the pressure of the pressurized draining gas in the pressurized draining gas injection line.

28. The system for the reception and transfer of a biopharmaceutical fluid under controlled pressure according to claim 27, wherein the means intended and suitable for supplying a pressurized draining gas supplies the draining gas at a pressure equal to at least 70 mbar.

29. The system for the reception and transfer of a biopharmaceutical fluid under controlled pressure according to claim 27, without a pump, such as peristaltic pump, connected to the drain tube or the drain outlet of the inner container of biopharmaceutical fluid.

30. A method for the reception and transfer of a biopharmaceutical fluid under controlled pressure, wherein:
a system is provided for the reception and transfer of a biopharmaceutical fluid under controlled pressure, said system comprising:
a device for the reception and then the draining of a biopharmaceutical fluid under controlled pressure, said device comprising:
an inner bag made of plastic, flexible and fluidtight, having an inner container intended and suitable for receiving a quantity at least equal to about 10 liters of biopharmaceutical fluid and provided with a filling port for supplying the biopharmaceutical fluid and a drain port for emptying the biopharmaceutical fluid, and connected in a fluidtight manner to the filling port and drain port, a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid,
an outer container into which the inner bag is placed, a compression chamber being formed between the outer container and the inner bag for which the filling inlet and drain outlet are located externally to the outer container, a port for injecting pressurized draining gas into the compression chamber being provided on said outer container,
fluidtight passages through the outer container via the filling tube and drain tube,
an integrated means for bleeding the gas filling the filling line prior to filling with biopharmaceutical fluid, so that this gas does not enter the inner bag,
the respective deformation capacities of the inner bag and outer container being chosen such that when injecting the pressurized draining gas into the compression chamber, the inner bag is compressed and the pressure causes the biopharmaceutical fluid contained therein to empty through the drain outlet, and
a means with pressure loss such as a filter associated in fluid communication with the drain tube or drain outlet of the inner container of biopharmaceutical fluid,
wherein:
the outer container comprises a fluidtight outer receptacle made of plastic, forming an outer chamber into which the inner bag is placed, defining the compression chamber, and comprising the injection port for the pressurized draining gas,
the filling tube and drain tube pass through the outer receptacle via fixed permanent connections, the filling inlet and drain outlet being located externally to the outer receptacle, and
the outer receptacle and the inner bag form a coherent whole that is disposable,
a means intended and suitable for supplying a pressurized draining gas, having a pressurized draining gas injection line adapted to be association in fluid communication or associated in fluid communication with the pressurized draining gas injection inlet or port of said device, and
a means for monitoring and controlling the pressure of the pressurized draining gas in the pressurized draining gas injection line,
said system being provided in the state that is empty of biopharmaceutical fluid and of pressurized draining gas, and a biopharmaceutical fluid to be received and transferred under controlled pressure is also provided,
providing a filling line and a drain line,
when the biopharmaceutical fluid is to be received in the device, first the integrated means for bleeding the gas filling the filling line is used, thus bleeding the gas filling the filling line, then the inner container of the inner bag is filled with biopharmaceutical fluid via the filling inlet, next the filling inlet is placed in the closed state, the drain outlet being in the closed state, and biopharmaceutical fluid is left in the inner container of the inner bag as long as desired, and
when it is desired to transfer the biopharmaceutical fluid from the inner container under controlled pressure:
the injection line for pressurized draining gas and the injection inlet for pressurized draining gas of the outer receptacle are connected in fluid communication and the drain outlet is placed in the open state, and
then the pressurized draining gas is injected into the compression chamber between the outer receptacle and the inner bag, the pressure compressing the inner bag and causing the biopharmaceutical fluid contained therein to drain out.

31. The method for the reception and transfer of a biopharmaceutical fluid under controlled pressure according to claim 30, wherein a means with pressure loss such as a filter is associated in fluid communication with the drain tube or drain outlet of the inner container of biopharmaceutical fluid.

32. The method for the reception and transfer of a biopharmaceutical fluid under controlled pressure according to claim 30, wherein, while draining, the drain port is placed towards the lower portion of the inner bag, in particular the lowermost portion of the inner bag.

33. The method for the reception and transfer of a biopharmaceutical fluid under controlled pressure according to claim 30, wherein the draining gas is injected such that the pressure of the biopharmaceutical fluid in the drain outlet is substantially constant throughout the draining.

34. The method for the reception and transfer of a biopharmaceutical fluid under controlled pressure according to claim 30, wherein the draining gas is supplied at a pressure equal to at least 70 mbar.

35. The method for the reception and transfer of a biopharmaceutical fluid under controlled pressure according to claim 30, wherein use is made of an integrated means for bleeding the gas filling the filling line comprising a bag for initial draining, an extrinsic fluid connection to the filling tube, an opening/closing device on the extrinsic fluid connection, and an opening/closing device on the filling tube, and wherein in order to bleed the gas filling the filling line prior to filling with biopharmaceutical fluid, the opening/closing device on the filling tube is closed, then while the opening/closing device on the extrinsic fluid connection is open the filling with biopharmaceutical fluid begins, and when the biopharmaceutical fluid reaches the extrinsic fluid connection the opening/closing device on the extrinsic fluid connection is closed and the opening/closing device on the filling tube is opened.

36. The method for the reception and transfer of a biopharmaceutical fluid under controlled pressure according to claim 30, wherein use is made of a device for the reception and then the draining of a biopharmaceutical fluid under controlled pressure wherein the outer container comprises a flexible outer bag and an external containment means, the outer bag being placed within the external containment means to limit the expansion capacity of the outer bag when pressurized draining gas is being injected into the compression chamber.

37. The device for the reception and then the draining of a biopharmaceutical fluid under controlled pressure according to claim 2, wherein the outer container consists of the outer receptacle.

38. The device for the reception and then the draining of a biopharmaceutical fluid under controlled pressure according to claim 37, wherein the outer receptacle is a flexible outer bag that is non-expandable or expandable with a limited capacity for expansion.

39. The device for the reception and then the draining of a biopharmaceutical fluid under controlled pressure according to claim 37, wherein the outer receptacle is a rigid or semi-rigid shell.

40. The device for the reception and then the draining of a biopharmaceutical fluid under controlled pressure according to claim 2, wherein the outer container comprises the outer receptacle which is a flexible outer bag, possibly expandable, and an external containment means adapted to receive the outer bag and able to limit the expansion capacity of the outer bag when the pressurized draining gas is being injected into the compression chamber.

41. The device for the reception and then the draining of a biopharmaceutical fluid under controlled pressure according to claim 40, wherein the containment means comprises two rigid and parallel main walls spaced apart from one another, in particular at a fixed distance, between which is placed the outer bag comprising two main walls on opposite sides.

42. The device for the reception and then the draining of a biopharmaceutical fluid under controlled pressure according to claim 41, wherein the free space at the periphery of the two rigid main walls serves as a passage for placing the outer bag or removing it from between the two main walls.

43. The device for the reception and then the draining of a biopharmaceutical fluid under controlled pressure according to claim 41, wherein the containment means also comprises one or more rigid side walls, rigidly connecting the two main walls.

44. The device for the reception and then the draining of a biopharmaceutical fluid under controlled pressure according to claim 2, further comprising, or adapted to be associated with, a means adapted such that, at least during draining, the drain port is located towards the lower portion of the inner bag, in particular the lowermost portion of the inner bag.

45. The device for the reception and then the draining of a biopharmaceutical fluid under controlled pressure according to claim 44, wherein the means adapted such that the drain port is located towards the lower portion of the inner bag is either a means for suspending the device on the end opposite the drain port or a means for tilting the containment means that the outer container comprises.

46. The device for the reception and then the draining of a biopharmaceutical fluid under controlled pressure according to claim 2, wherein the integrated means for bleeding the gas filling the filling line prior to filling with biopharmaceutical fluid is a bag for initially draining the gas filling the filling line, connected by an extrinsic fluid connection to the filling tube, near the inner bag, an opening/closing device being provided on the extrinsic fluid connection and an opening/closing device being provided on the filling tube near the connection to the extrinsic fluid connection and between the latter and the inner bag.

47. The device for the reception and then the draining of a biopharmaceutical fluid under controlled pressure according to claim 2, wherein the filling tube and drain tube pass through the wall of the outer receptacle from one side to the other via fluidtight and fixed permanent connections, welded or the like, formed in an end edge section of this wall by two facing areas of this wall, some portions flat against one another, other portions trapping the filling tube and drain tube between them in a snug fit.

48. The device for the reception and then the draining of a biopharmaceutical fluid under controlled pressure according to claim 2, wherein the wall of the inner bag comprises an end edge section where the filling port and drain port are located adjacent to one another, and the filling tube and drain tube are located adjacent to one another.

49. The device for the reception and then the draining of a biopharmaceutical fluid under controlled pressure according to claim 2, wherein the filling tube and drain tube pass through the wall of the inner bag from the outer side via fluidtight and fixed permanent connections, welded or the like, formed in an end edge section of this wall by two facing areas of this wall, some portions flat against one another, other portions trapping the filling tube and drain tube between them in a snug fit.

50. The device for the reception and then the draining of a biopharmaceutical fluid under controlled pressure according to claim 2, wherein the filling tube and drain tube pass through the wall of the outer receptacle from one side to the other in an end edge section of this wall and pass through the wall of the inner bag from the outer side in an end edge section of that wall, the end edge section of the wall of the outer receptacle and the end edge section of the inner bag extending generally parallel to one another and positioned adjacent to one another.

51. The device for the reception and then the draining of a biopharmaceutical fluid under controlled pressure according to claim 2, wherein the filling tube and drain tube pass through the wall of the outer receptacle from one side to the other in an end edge section of this wall and pass through the wall of the inner bag from the outer side in an end edge section of that wall, the end edge section of the wall of the outer receptacle and the end edge section of the inner bag being arranged next to one another, the section of filling tube and the section of draining tube that are located between the end edge section of the wall of the outer receptacle and the end edge section of the inner bag being self-supporting and supporting the inner bag.

52. The device for the reception and then the draining of a biopharmaceutical fluid under controlled pressure according to claim 2, wherein the port for injecting pressurized draining gas, which is connected in particular to an injection tube having an injection inlet, is arranged in the wall of the outer receptacle with a fluidtight and fixed permanent connection, by welding or the like, formed in an end edge section of this wall by two facing areas of this wall, some portions flat against one another, other portions defining between them the injection port, in particular trapping the injection tube between them in a snug fit.

53. The device for the reception and then the draining of a biopharmaceutical fluid under controlled pressure according to claim 2, wherein the wall of the outer receptacle comprises an end edge section where the filling tube, the drain tube, the injection port, in particular the injection tube, are located adjacent to one another.

54. The device for the reception and then the draining of a biopharmaceutical fluid under controlled pressure according to claim 2, wherein, aside from the section of filling tube and the section of drain tube which are located between the end edge section of the wall of the outer receptacle and the end edge section of the inner bag which are arranged next to one another, the inner bag is mounted so as to be unrestrained within the outer receptacle.

55. The device for the reception and then the draining of a biopharmaceutical fluid under controlled pressure according to claim 2, wherein, when the draining gas is injected into the compression chamber, the wall of the inner bag and the wall of the outer receptacle the compression chamber are spaced apart from one another along all or substantially all their lateral periphery.

56. The device for the reception and then the draining of a biopharmaceutical fluid under controlled pressure according to claim 2, wherein the inner bag has a wall comprising two main wall portions opposite one another and the outer receptacle is a bag in which the wall comprises two main wall portions opposite one another, such that when the inner bag and the bag of the outer receptacle are empty, the respective walls and thus the bags themselves can be folded flat in a layered arrangement.

57. The device for the reception and then the draining of a biopharmaceutical fluid under controlled pressure according to claim 2, wherein the outer receptacle is at least partially transparent to allow viewing the inner bag through the wall.

58. The device for the reception and then the draining of a biopharmaceutical fluid under controlled pressure according to claim 2, wherein the deployed inner bag has a capacity of between 8 liters and 60 liters, in particular about 10 to 50 liters, while the deployed outer receptacle has a capacity at least equal to that of the deployed inner bag, in particular at least equal to about 50 liters for a deployed inner bag having a capacity of about 10.

59. The device for the reception and then the draining of a biopharmaceutical fluid under controlled pressure according to claim 2, comprising a means with pressure loss such as a filter associated in fluid communication with the drain tube or the drain outlet of the inner container of biopharmaceutical fluid.

60. The device for the reception and then the draining of a biopharmaceutical fluid under controlled pressure according to claim 2, wherein the drain tube or the drain outlet of the inner container of biopharmaceutical fluid is without a pump such as a peristaltic pump.

61. A system for the reception and transfer of a biopharmaceutical fluid under controlled pressure, comprising:
   a device for the reception and then the draining of a biopharmaceutical fluid under controlled pressure according to claim 2, in particular comprising a means with pressure loss such as a filter associated in fluid communication with the drain tube or drain outlet of the inner container of biopharmaceutical fluid,
   a means intended and suitable for supplying a pressurized draining gas, having a pressurized draining gas injection line adapted to be association in fluid communication or associated in fluid communication with the pressurized draining gas injection inlet or port of said device, and
   a means for monitoring and controlling the pressure of the pressurized draining gas in the pressurized draining gas injection line.

62. The system for the reception and transfer of a biopharmaceutical fluid under controlled pressure according to claim 61, wherein the means intended and suitable for supplying a pressurized draining gas supplies the draining gas at a pressure equal to at least 70 mbar.

63. The system for the reception and transfer of a biopharmaceutical fluid under controlled pressure according to claim 61, without a pump, such as peristaltic pump, connected to the drain tube or the drain outlet of the inner container of biopharmaceutical fluid.

64. A method for the reception and transfer of a biopharmaceutical fluid under controlled pressure, wherein:
   a system is provided for the reception and transfer of a biopharmaceutical fluid under controlled pressure, said system comprising:
      a device for the reception and then the draining of a biopharmaceutical fluid under controlled pressure, said device comprising:
         an inner bag made of plastic, flexible and fluidtight, having an inner container intended and suitable for receiving the biopharmaceutical fluid and provided with a filling port for supplying the biopharmaceutical fluid and a drain port for emptying the biopharmaceutical fluid, and connected in a fluidtight manner to the filling port and drain port,
         a filling tube having an inlet for filling the inner container with biopharmaceutical fluid, adapted to be connected to a filling line for the biopharmaceutical fluid, and a drain tube having an outlet for draining the inner container of biopharmaceutical fluid, adapted to be connected to a drain line for the biopharmaceutical fluid, an outer container comprising a fluidtight outer receptacle made of plastic, forming an outer chamber into which the inner bag is placed, its filling inlet and drain outlet (12) being located externally to the outer container, defining a compression chamber between the outer container and the inner bag, a port for injecting pressurized draining gas into the compression chamber being provided on said outer container, the filling tube and drain tube passing through the outer receptacle via fluidtight and fixed permanent connections, the respective deformation capacities of the inner bag and outer container being chosen such that when injecting the pressurized draining gas into the compression chamber, the inner bag is compressed and the pressure causes the biopharmaceutical fluid contained therein to empty through the drain outlet, an integrated means for bleeding the gas filling the filling line prior to filling with biopharmaceutical fluid, so that this gas does not enter the inner bag, the outer receptacle and the inner bag forming a coherent whole that is disposable, and a means with pressure loss such as a filter associated in fluid communication with the drain tube or drain outlet of the inner container of biopharmaceutical fluid, and wherein:
the inner bag is intended and suitable for receiving an amount at least equal to about 10 liters of biopharmaceutical fluid, and the outer receptacle when deployed has a capacity of at least 40 liters, and the device comprises a section of filling tube and a section of drain tube which are located between the end edge section of the inner bag to which they are adjacent and the end edge section of the wall of the outer receptacle through which they pass via fluidtight and fixed permanent connections, the end edge section of the inner bag and the end edge section of the wall of the outer receptacle being arranged next to and offset from one another, a means intended and suitable for supplying a pressurized draining gas, having a pressurized draining gas injection line adapted to be association in fluid communication or associated in fluid communication with the pressurized draining gas injection inlet or port of said device, and a means for monitoring and controlling the pressure of the pressurized draining gas in the pressurized draining gas injection line, the system being provided in the state that is empty of biopharmaceutical fluid and of pressurized draining gas, and a biopharmaceutical fluid to be received and transferred under controlled pressure is also provided, providing of a filling line and a drain line
when the biopharmaceutical fluid is to be received in the device, first the integrated means for bleeding the gas filling the filling line is used, thus bleeding the gas filling the filling line, then the inner container of the inner bag is filled with biopharmaceutical fluid via the filling inlet, next the filling inlet is placed in the closed state, the drain outlet being in the closed state, and biopharmaceutical fluid is left in the inner container of the inner bag as long as desired, and when it is desired to transfer the biopharmaceutical fluid from the inner container under controlled pressure:
the injection line for pressurized draining gas and the injection inlet for pressurized draining gas of the outer receptacle are connected in fluid communication and the drain outlet is placed in the open state, and then the pressurized draining gas is injected into the compression chamber between the outer receptacle and the inner bag, the pressure compressing the inner bag and causing the biopharmaceutical fluid contained therein to drain out.

65. The method for the reception and transfer of a biopharmaceutical fluid under controlled pressure according to claim 64, wherein a means with pressure loss such as a filter is associated in fluid communication with the drain tube or drain outlet of the inner container of biopharmaceutical fluid.

66. The method for the reception and transfer of a biopharmaceutical fluid under controlled pressure according to claim 64, wherein, while draining, the drain port is placed towards the lower portion of the inner bag, in particular the lowermost portion of the inner bag.

67. The method for the reception and transfer of a biopharmaceutical fluid under controlled pressure according to claim 64, wherein the draining gas is injected such that the pressure of the biopharmaceutical fluid in the drain outlet is substantially constant throughout the draining.

68. The method for the reception and transfer of a biopharmaceutical fluid under controlled pressure according to claim 64, wherein the draining gas is supplied at a pressure equal to at least 70 mbar.

69. The method for the reception and transfer of a biopharmaceutical fluid under controlled pressure according to claim 64, wherein use is made of an integrated means for bleeding the gas filling the filling line comprising a bag for initial draining, an extrinsic fluid connection to the filling tube, an opening/closing device on the extrinsic fluid connection, and an opening/closing device on the filling tube, and wherein in order to bleed the gas filling the filling line prior to filling with biopharmaceutical fluid, the opening/closing device on the filling tube is closed, then while the opening/closing device on the extrinsic fluid connection is open the filling with biopharmaceutical fluid begins, and when the biopharmaceutical fluid reaches the extrinsic fluid connection the opening/closing device on the extrinsic fluid connection is closed and the opening/closing device on the filling tube is opened.

70. The method for the reception and transfer of a biopharmaceutical fluid under controlled pressure according to claim 64, wherein use is made of a device for the reception and then the draining of a biopharmaceutical fluid under controlled pressure wherein the outer container comprises a flexible outer bag and an external containment means, the outer bag being placed within the external containment means to limit the expansion capacity of the outer bag when pressurized draining gas is being injected into the compression chamber.

* * * * *